(12) United States Patent
Sholev

(10) Patent No.: US 10,835,108 B2
(45) Date of Patent: Nov. 17, 2020

(54) CONTROL UNIT FOR A FLEXIBLE ENDOSCOPE

(71) Applicant: Human Xtensions Ltd., Netanya (IL)

(72) Inventor: Mordehai Sholev, Moshav Amikam (IL)

(73) Assignee: Human Xtensions Ltd., Netanya (IL)

( * ) Notice: Subject to any disclaimer, the term of this patent is extended or adjusted under 35 U.S.C. 154(b) by 312 days.

(21) Appl. No.: 15/565,177

(22) PCT Filed: Aug. 11, 2016

(86) PCT No.: PCT/IL2016/050879
§ 371 (c)(1),
(2) Date: Oct. 9, 2017

(87) PCT Pub. No.: WO2017/025969
PCT Pub. Date: Feb. 16, 2017

(65) Prior Publication Data
US 2018/0098687 A1    Apr. 12, 2018

Related U.S. Application Data

(60) Provisional application No. 62/203,421, filed on Aug. 11, 2015.

(51) Int. Cl.
*A61B 1/00* (2006.01)
*A61B 1/005* (2006.01)
(Continued)

(52) U.S. Cl.
CPC ........ *A61B 1/00133* (2013.01); *A61B 1/0016* (2013.01); *A61B 1/0052* (2013.01);
(Continued)

(58) Field of Classification Search
CPC combination set(s) only.
See application file for complete search history.

(56) References Cited

U.S. PATENT DOCUMENTS 8,100,825 B2    1/2012  Moriyama
8,409,080 B2 *  4/2013  Gumbs ................ A61B 1/0016
                                                    600/118
(Continued)

FOREIGN PATENT DOCUMENTS

CN    101056574    10/2007
CN    103619230     3/2014
(Continued)

OTHER PUBLICATIONS

Notification of Office Action and Search Report dated Jan. 18, 2019 From the State Intellectual Property Office of the People's Republic of China Re. Application No. 201680029036 and Its Translation into English.) (17 Pages).

(Continued)

*Primary Examiner* — John P Leubecker
*Assistant Examiner* — Shankar Raj Ghimire

(57) ABSTRACT

A control unit attachable to a flexible endoscope having a shaft deflectable via two rotatable knobs is provided. The control unit includes a user interface including a first interface being mounted on a pivotal support attached to a housing of the control unit, the first interface being engageable by a palm of a hand. The control unit further includes a drive unit operable via the user interface, the drive unit including a first drive mechanism for engaging the two rotatable knobs thereby allowing a user to control deflection of the shaft of the endoscope via the first interface.

13 Claims, 8 Drawing Sheets

(51) Int. Cl.
  *A61B 17/29* (2006.01)
  *A61M 25/01* (2006.01)
  *A61B 1/045* (2006.01)
  *A61B 17/00* (2006.01)

(52) U.S. Cl.
  CPC .......... *A61B 1/00066* (2013.01); *A61B 1/045* (2013.01); *A61B 17/29* (2013.01); *A61M 25/0136* (2013.01); *A61B 2017/003* (2013.01); *A61B 2017/0034* (2013.01); *A61B 2017/00398* (2013.01); *A61B 2017/00424* (2013.01); *A61B 2017/291* (2013.01)

(56) References Cited

U.S. PATENT DOCUMENTS

| | | | | |
|---|---|---|---|---|
| 8,419,623 | B2 * | 4/2013 | Garcia | A61B 1/00105 600/136 |
| 8,543,240 | B2 * | 9/2013 | Itkowitz | G06F 3/014 414/2 |
| 9,649,096 | B2 * | 5/2017 | Sholev | A61B 17/29 |
| 2002/0171625 | A1 | 11/2002 | Rothchild | |
| 2007/0238927 | A1 * | 10/2007 | Ueno | A61B 1/00105 600/145 |
| 2008/0119696 | A1 * | 5/2008 | Moriyama | A61B 1/0052 600/146 |
| 2011/0065994 | A1 * | 3/2011 | Kudoh | A61B 1/0051 600/146 |
| 2012/0130401 | A1 * | 5/2012 | Barrier | A61B 17/2909 606/130 |
| 2012/0165829 | A1 | 6/2012 | Chen et al. | |
| 2012/0277762 | A1 * | 11/2012 | Lathrop | A61B 34/70 606/130 |
| 2013/0060088 | A1 | 3/2013 | Okamoto | |
| 2013/0190566 | A1 * | 7/2013 | Miyoshi | A61B 1/0057 600/131 |
| 2013/0317522 | A1 * | 11/2013 | Nishizawa | A61B 17/2909 606/130 |
| 2014/0025089 | A1 * | 1/2014 | Sholev | A61B 17/29 606/130 |
| 2014/0275763 | A1 | 9/2014 | King et al. | |
| 2015/0031953 | A1 * | 1/2015 | Atarot | A61B 1/00133 600/118 |
| 2015/0148602 | A1 * | 5/2015 | Hill | A61B 1/00154 600/109 |
| 2015/0359415 | A1 * | 12/2015 | Lang | A61B 1/0052 600/141 |
| 2016/0089125 | A1 * | 3/2016 | Morimoto | A61B 8/12 600/107 |
| 2016/0166129 | A1 * | 6/2016 | Walish | A61B 1/0052 600/104 |
| 2016/0271385 | A1 * | 9/2016 | Sterlina | H01R 39/08 |
| 2017/0086651 | A1 * | 3/2017 | Sato | A61B 1/00114 |
| 2017/0215697 | A1 * | 8/2017 | Hatano | G02B 23/24 |
| 2017/0215705 | A1 * | 8/2017 | Yamaya | A61B 1/00121 |
| 2017/0280973 | A1 * | 10/2017 | Hatano | G02B 23/24 |

FOREIGN PATENT DOCUMENTS

| | | | |
|---|---|---|---|
| EP | 1769722 | 4/2007 | |
| GB | 2070715 | 9/1981 | |
| JP | 02-055907 | 2/1990 | |
| JP | 05-300873 | 11/1993 | |
| JP | 2003-010112 | 1/2003 | |
| JP | 2007-089808 | 4/2007 | |
| WO | WO-2012127462 A1 * | 9/2012 | ......... A61B 17/2909 |
| WO | WO 2015/029041 | 3/2015 | |
| WO | WO 2015/038290 | 3/2015 | |
| WO | WO-2015029041 A1 * | 3/2015 | ......... A61B 17/2909 |
| WO | WO 2017/025969 | 2/2017 | |

OTHER PUBLICATIONS

International Preliminary Report on Patentability dated Feb. 22, 2018 From the International Bureau of WIPO Re. Application No. PCT/IL2016/050879. (6 Pages).

Supplementary European Search Report and the European Search Opinion dated Apr. 12, 2019 From the European Patent Office Re. Application No. 16834773.0. (7 Pages).

Notification of Office Action dated Jul. 25, 2019 From the National Intellectual Property Administration of the People's Republic of China Re. Application No. 201680029036 and Its Translation Into English. (9 Pages).

International Search Report and the Written Opinion dated Jan. 13, 2017 From the International Searching Authority Re. Application No. PCT/IL2016/050879. (10 Pages).

Notification of Office Action dated Jan. 8, 2020 From the National Intellectual Property Administration of the People's Republic of China Re. Application No. 201680029036 and Its Translation Into English. (16 Pages).

Examination Report dated Apr. 14, 2020 From the Australian Government, IP Australia Re. Application No. 2016306164. (3 Pages).

Notice of Reasons for Rejection dated Aug. 4, 2020 From the Japan Patent Office Re. Application No. 2017-560595 and Its Translation Into English. (5 Pages).

\* cited by examiner

CONTROL UNIT FOR A FLEXIBLE ENDOSCOPE

RELATED APPLICATIONS

This application is a National Phase of PCT Patent Application No. PCT/IL2016/050879 having International filing date of Aug. 11, 2016, which claims the benefit of priority under 35 USC § 119(e) of U.S. Provisional Patent Application No. 62/203,421 filed on Aug. 11, 2015. The contents of the above applications are all incorporated by reference as if fully set forth herein in their entirety.

FIELD AND BACKGROUND OF THE INVENTION

The present invention relates to a control unit that is attachable to a flexible endoscope and can be used to control both tip deflection and a working channel-positioned tool using a single hand.

Flexible endoscopes (FIG. 1) consist of a control head and a flexible shaft with a maneuverable tip. The head is connected to a light source via an 'umbilical' cord, through which pass other tubes transmitting air, water and suction, etc. The working channel is used for the passage of diagnostic or therapeutic tools.

Two side-by-side mounted rotatable knobs are mounted on the side of the control head and are used for up/down and right/left movement of the shaft tip.

In experienced hands, these knobs can be used to control the angle of the tip in any direction, however, such control requires use of both hands rendering simultaneous control over any other instrument (e.g. diagnostic or therapeutic tool positioned through the working channel) impossible. To traverse this limitation, the control knobs of standard flexible endoscopes incorporate a friction braking system, so that the tip can be fixed temporarily in any desired position thus freeing the operator to control other instruments.

Although such a solution enables control of a diagnostic or therapeutic tool positioned through a working channel when the endoscope tip is locked in a specific position, it does not enable endoscope tip repositioning while maintaining control over the tool. The latter is important in cases where a procedure requires maneuvering of an endoscope camera and tool simultaneously.

In order to address this limitation of standard flexible endoscopes, the present inventor devised a control unit, which enables an operator to control the tip of a flexible endoscope as well as a tool positioned through the working channel thereof using a single hand.

SUMMARY OF THE INVENTION

According to one aspect of the present invention, there is provided a control unit attachable to an endoscope having a shaft deflectable via two rotatable knobs, the control unit comprising: (a) a user interface including a first interface being mounted on a pivotal support attached to a housing of the control unit, the first interface being engageable by a palm of a hand; and (b) a drive unit operable via the user interface, the drive unit including a first drive mechanism for engaging the two rotatable knobs thereby allowing a user to control deflection of the shaft of the endoscope via the first interface.

According to further features in preferred embodiments of the invention described below, a first rotatable knob of the two rotatable knobs controls up/down deflection of the shaft and a second rotatable knob of the two rotatable knobs controls left/right deflection of the shaft and further wherein the first interface controls both up/down and left/right deflection of the shaft.

According to still further features in the described preferred embodiments, the first drive mechanism includes at least one motor operable via the first interface.

According to still further features in the described preferred embodiments, the at least one motor operates the two knobs.

According to still further features in the described preferred embodiments, the drive mechanism includes a set of gears interposed between the at least one motor and the two knobs.

According to still further features in the described preferred embodiments, the drive unit further comprises a second drive mechanism for engaging a manually operable end of a surgical tool positionable through a working channel of the endoscope.

According to still further features in the described preferred embodiments, the control unit further comprises a second interface being pivotally attached to the first interface and being engageable by one or more fingers of the hand, the second interface being for operating the surgical tool through the second drive mechanism.

According to still further features in the described preferred embodiments, the control unit further comprises a restraint being pivotally attached to the first interface and having an element capable of elastically deforming to apply a restraining force to a back of the hand when the palm is engaged with the first interface.

According to still further features in the described preferred embodiments, the pivotal support is gimbaled.

According to still further features in the described preferred embodiments, the second interface includes pads simultaneously operable via thumb and index finger of the hand.

According to still further features in the described preferred embodiments, the second drive mechanism includes a servo.

According to still further features in the described preferred embodiments, the control unit further comprising a third interface for wirelessly controlling a remote device.

According to still further features in the described preferred embodiments, the surgical tool includes a steerable shaft and an effector end controllable via the second interface.

The present invention successfully addresses the shortcomings of the presently known configurations by providing a control unit for a flexible endoscope, which enables an operator to control the endoscope as well as a tool mounted therein via a single hand.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the Drawings.

DESCRIPTION OF THE PREFERRED EMBODIMENTS

Figure 1:
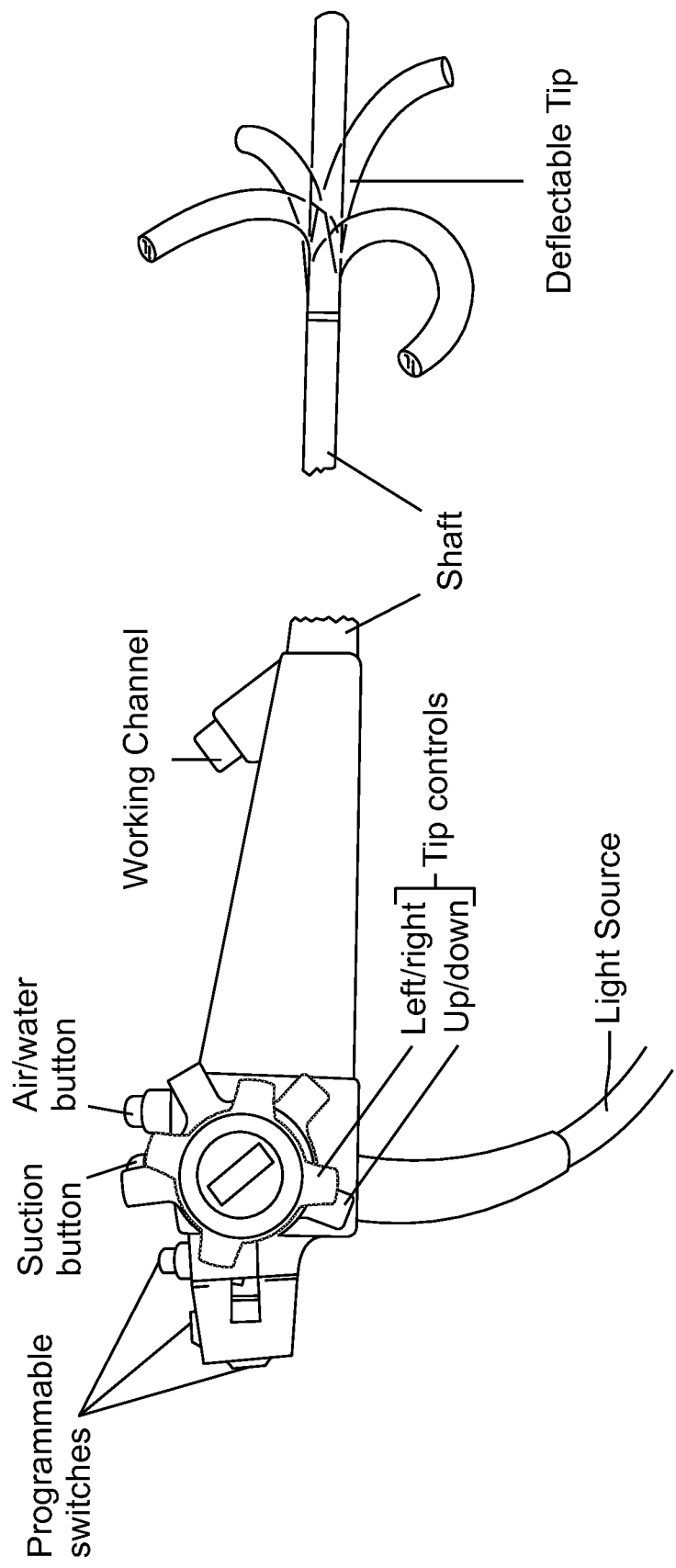
FIG. 1 is a prior art drawing of a standard flexible endoscope.

The present invention is of a control unit which can be used to control the movement of a flexible endoscope tip, as well as the movement and function of a tool positioned through a working channel thereof.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Endoscopic procedures require a surgeon to control both the endoscope and its associated tools (e.g. working channel tools). Since standard flexible endoscopes require both hands for tip deflection control, a surgeon cannot simultaneously control both endoscope and a surgical/therapeutic tool positioned through a working channel thereof.

While reducing the present invention to practice, the present inventor devised a control unit which can be attached to a standard flexible endoscope and enable a surgeon to control both endoscope and a diagnostic/therapeutic tool (as well as other additional peripheral tools) using a single hand. As is further described herein, the control unit of the present invention can be retrofitted onto any flexible endoscope without modifications to the endoscope control head.

Thus, according to one aspect of the present invention there is provided a control unit for a standard flexible endoscope. As used herein, the term "standard flexible endoscope" encompasses any endoscope with a deflectable tip controllable via rotatable knobs. Such an endoscope preferably includes a camera for imaging an anatomical region of interest.

The control unit includes a drive unit with attached user interface. As is further described hereinunder, the interface is operated by a single hand of a user and actuates motors and gears/levers/wires within the control unit to thereby control the endoscope and diagnostic/therapeutic tool positioned therethrough.

The user interface has separate controls for endoscope tip deflection and the diagnostic/therapeutic tool. The user interface includes a first interface which is mounted on a pivotal support (e.g. gimbaled) attached to a housing of the control unit. The first interface is engageable by a palm of a hand and enables the user to control deflection of the endoscope tip in any direction via a first drive mechanism of the drive unit.

To maintain the palm of a user against the first interface through its operation, the control unit further includes a restraint, which forms a part of the first interface and includes an element that is capable of elastically deforming to apply a restraining force to a back of the hand (dorsum) when the palm is engaged with the first interface. When this restraint engages the back of the hand, the element elastically deforms and applies a downward force to the back of the hand thus maintaining the hand against the first interface and enabling precise control of this interface, as well as, enabling the user to pull up on the endoscope.

The control unit also includes a second interface, which is pivotally attached to the first interface and is engageable by one or more fingers of the hand. The second interface controls the operation of a tool positioned through the working channel and attached to a second drive mechanism of the drive unit. The second interface can control an effector end of the tool (e.g., opening and closing a grasper), rotate or translate the shaft thereof and/or deflect a steerable portion thereof.

The user interface of the present invention provides these three functions via movement of three separate limb joint and muscle groups:

(i) The endoscope is moved up and down and side to side with respect to body by arm movement (primarily about the elbow and/or shoulder joints).

(ii) The shaft of the endoscope is deflected via hand movement (primarily about the wrist joint). This is achieved by tilting the first interface.

(iii) The working channel tool is actuated via finger movement (primarily about the inter-phalangeal joints and the metacarpal-phalangeal joints). Finger movement can be used to operate the effector end of the tool, translate and roll the shaft and/or deflect a steerable portion of the shaft.

As is mentioned hereinabove, the control unit of the present invention engages the control knobs of the endoscope to thereby control deflection of the endoscope shaft via these knobs. Several approaches can be used to provide such functionality. For example, the user interface can be linked to the control knobs through a drive mechanism that includes gears, levers and/or wires which transfer the movement of the interface to rotation of the knob(s). The drive mechanism can be a simple mechanical 'linkage' or it can include one or motors/servos for enabling fine control as well as decreasing the interface force needed for knob rotation.

FIGS. 2a-6b illustrate one embodiment of the present control unit which is referred to herein as control unit 10. Control unit 10 utilizes motors and servos for transferring user hand and finger movements at the interface to deflection of the endoscope shaft and operation of a tool provided through the working channel thereof.

Figure 2B:
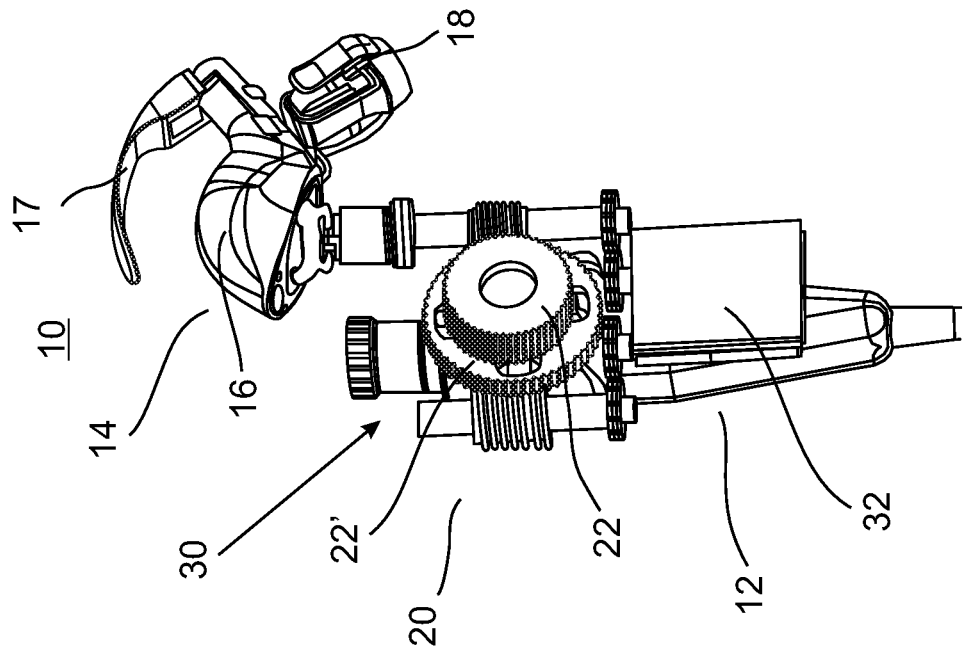
FIGS. 2a-b illustrate the present control unit mounted on an endoscope (FIG. 2a) and the interface and drive mechanism components of the control unit (FIG. 2b).
Figure 2A:
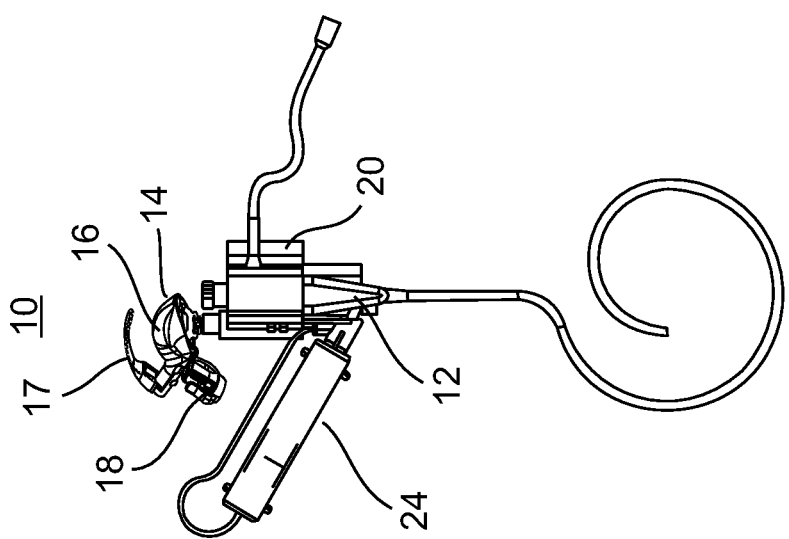

FIGS. 2a-b illustrate control unit 10 with attached endoscope 12. Control unit 10 includes a user interface 14 which includes a palm interface 16, dorsum interface 17 and a finger interface 18. Interface 14 will be described in greater detail below. Control unit 10 also includes a first drive mechanism 20 for translating movements of palm interface 16 to rotation of knobs 22 and 22' (FIG. 2b) of endoscope 12. Drive mechanism 20 is an electro-mechanical device, which utilizes motors and gears to rotate knobs 22 and 22'.

Control unit 10 further includes a second drive mechanism 24 for transforming movements of finger interface 18 into operation of a tool provided through the working channel of endoscope 12. Drive mechanism 24 is an electromechanical device that includes one or more motors/servos and gears to operate a manually operative end of a tool.

User interface 14 can include additional interface elements including buttons and levers which enable wireless (WiFi, BT) control over peripheral instruments including a monitor (for displaying the endoscope camera image), a computer (for displaying files related to a procedure) or lighting.

FIG. 2b illustrates control unit 10 with a portion of its housing removed to show gear cluster 30 and chip 32 that enable palm interface 16 to control the rotation of knobs 22.

Chip 32 is electrically connected to user interface 14 and receives position sensor information therefrom. This information is then translated by chip 32 to command signals for drive mechanisms 20 and 24. Chip 32 can also be connected to external devices via wireless communication modes to enable a surgeon to control peripheral devices via interface 14.

Figure 3:
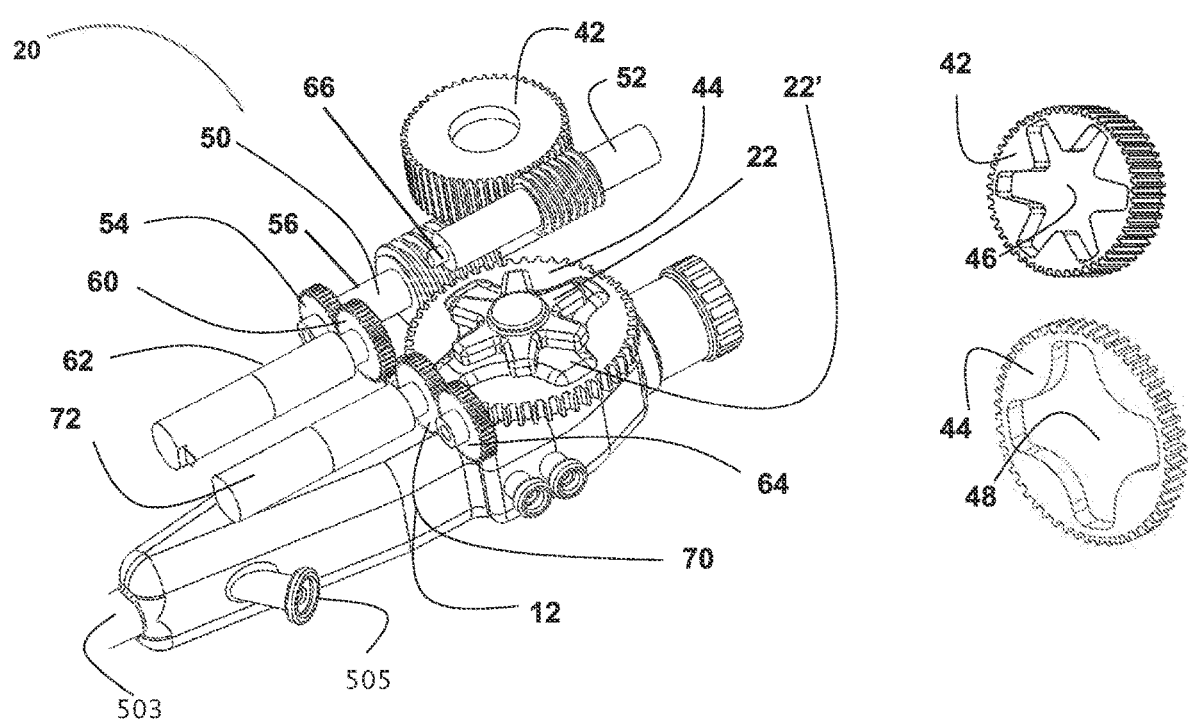
FIG. 3 illustrates the first drive mechanism for controlling the rotatable knobs of the endoscope.

FIG. 3 illustrates first drive mechanism 20 in greater detail. Gears 42 and 44 (also shown separately on right) have shaped holes 46 and 48 (respectively) to complement the shape of knobs 22' and 22 of endoscope 12 (respectively). Gear 42 is fixed around the wings of knob 22 while gear 44 is fixed around knob 22'. A worm gear 50 is coupled to gear 42; and a worm gear 52 is coupled to gear 44.

A gear 54 is fixed to a shaft 56 of worm gear 50 and engages a gear 60 driven by motor 62. Gear 64 is fixed to a shaft 66 (shown detached therefrom for clarity) of worm gear 52 and engages gear 70 driven by motor 72.

When chip 32 (FIG. 2b) detects a change in the orientation of palm interface 16, a signal is sent to motors 62 and/or 72 to actuate knobs 22 and/or 22' through the interconnecting gears.

Knobs 22 and 22' each articulates the distal end on a separate plane. The articulation planes of the distal end of the flexible endoscope are orthogonal, thus the combined movement of the distal end of the flexible tube produces spatial articulation allowing the surgeon to navigate the surgeon to a desired orientation.

Figure 4A:
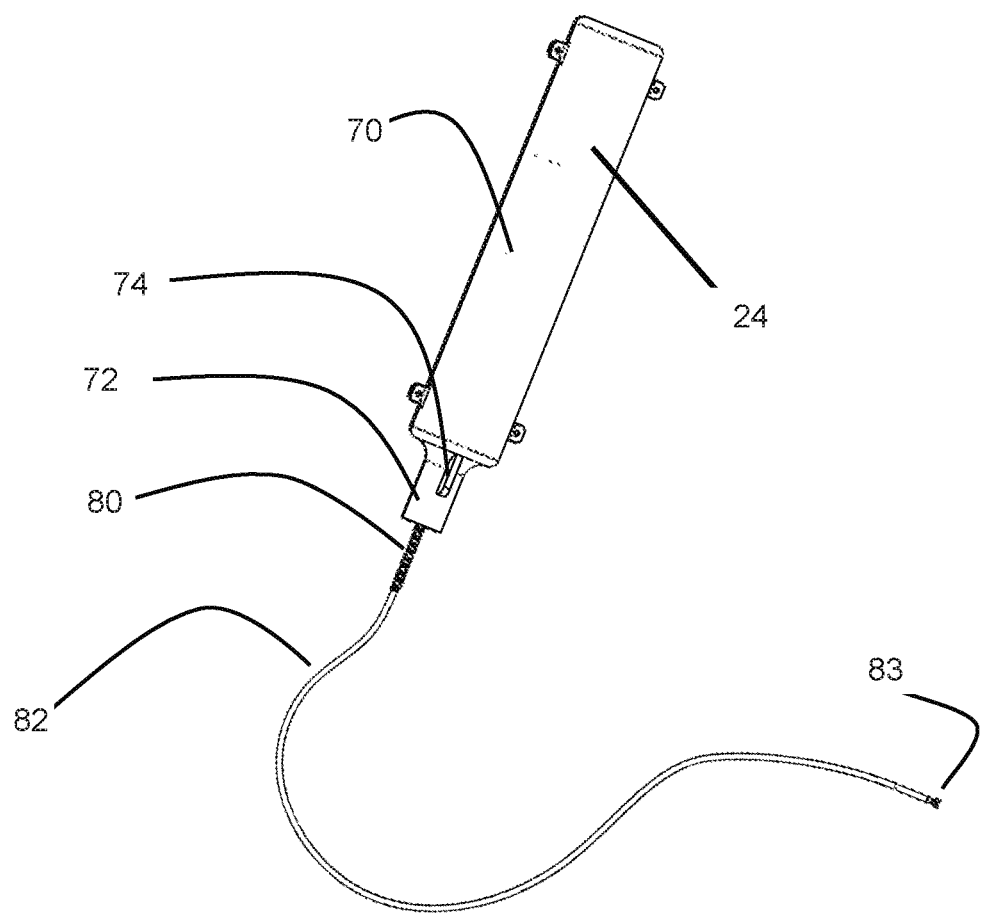
FIGS. 4a-b illustrate the second drive mechanism with attached tool.
Figure 4B:
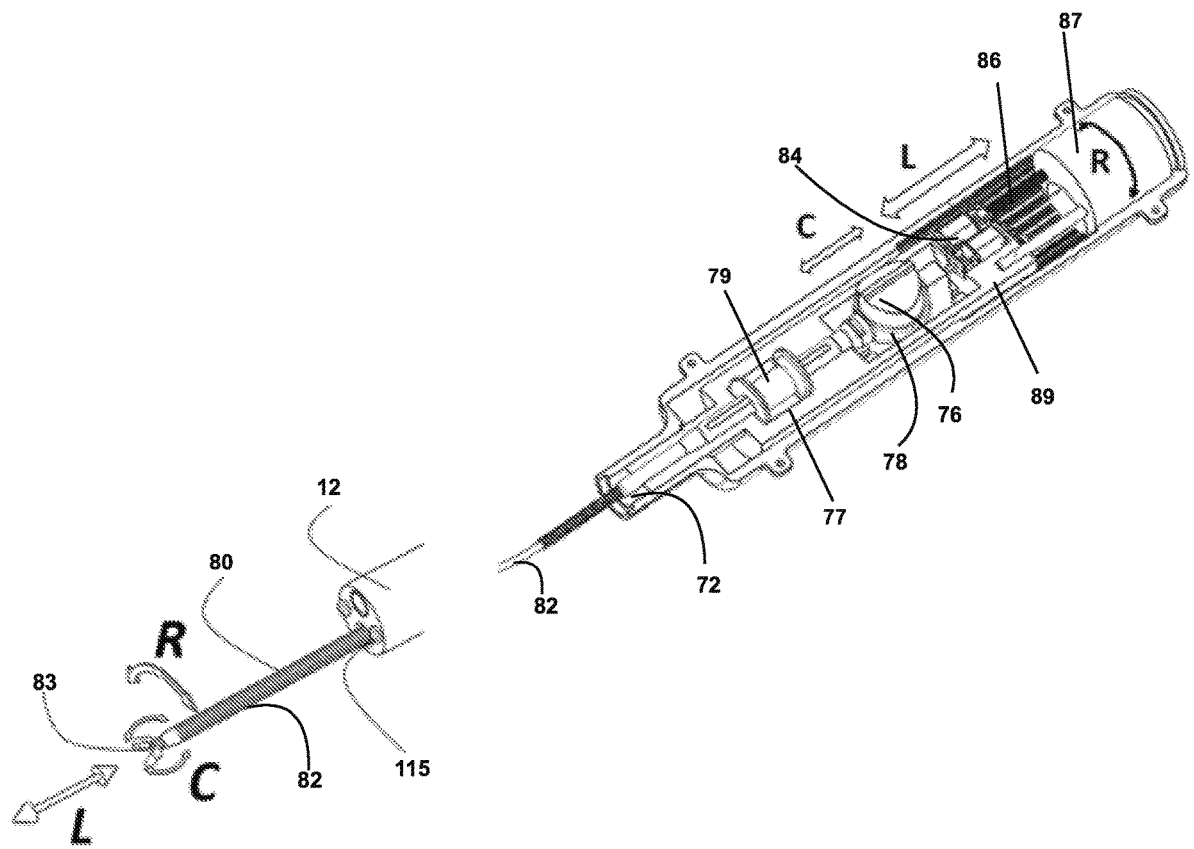

FIGS. 4a-b illustrate second drive mechanism 24, which is actuated by interface 18 in greater detail. Drive mechanism 24 includes a housing 70, which includes a neck region 72 and orientation wings 74. Wings 74 engage respective slots in control unit 10 to prevent housing 70 from freely rotating. Housing 70 can be fabricated from two halves, which are attached via screws, snaps and the like.

FIG. 4b illustrates the internal components of drive mechanism 24 and the distal end of endoscope 12 showing shaft 82 of tool 80 protruding from distal opening 115. The movements of components inside drive mechanism 24 are translated to movements of shaft 82 and grasper 83 as is indicated by R, L and C.

An engagement element 76 is designed for holding a manual control end of a diagnostic or surgical tool 80 positionable through a working channel 13 of endoscope 12. In this embodiment, element 76 is configured for holding a loop-type finger hold 78 of a tool 80 having grasper 83 effector end (FIG. 4a), while opening 77 is designed for holding a barrel-type finger hold 79 of tool 80. Moving finger hold 78 with respect to finger hold 79 opens and closes jaws 83 of tool 80.

Tool 80 is positioned with holds 76 and 79 as shown in FIG. 4b and shaft 82 positioned through a lumen in housing 70 and out from an opening at neck region 72.

Drive mechanism 24 is capable of 4 separate movements, rotating tool 80 (R) translating shaft 82 of tool 80 forwards and backwards 115 (L), and opening and closing the jaws of grasper 83 (C).

To open and close the jaws of grasper 83, drive mechanism 24 includes a motor 84 for driving a screw 86 into and out of a thread within cylinder 87. When the shaft of motor 84 rotates, screw 86 rotates into cylinder 87 thereby sliding finger hold 76 with respect to finger hold 79 (C).

Forward and backward movement of cylinder 87 (L) moves assembly 89 thus moving the entire tool 80 without actuating grasper 83. Such movement can be controlled by motor 84 or another motor.

An additional motor can rotate cylinder 87 thereby rotating tool 80 within drive mechanism 24.

A tool 80 having control wires for steering a portion thereof can also be connected to drive mechanism 24. The control wires of such a tool can be linked to one or more motors of drive mechanism 24 via, for example, gears and rods to enable the motor(s) to selectively pull one or more control wires and deflect a steerable portion of the tool.

As is mentioned hereinabove, user interface 14 of the present invention enables simultaneous control over endoscope tip deflection and tool operation using a single hand.

Figure 5B:
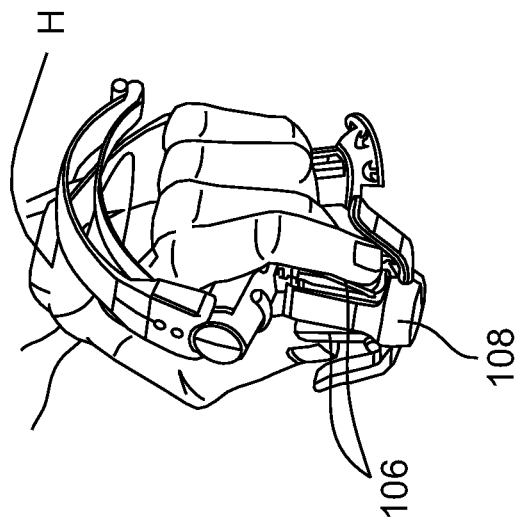
FIGS. 5a-b illustrate the various interfaces of the user interface of the present control unit (FIG. 5a) and their engagement to a user's hand (FIG. 5b).
Figure 5A:
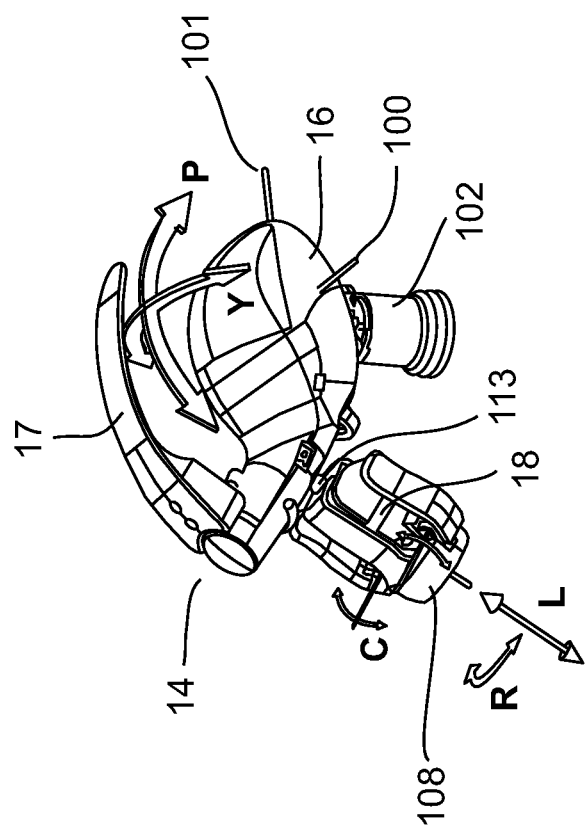
Figure 6A:
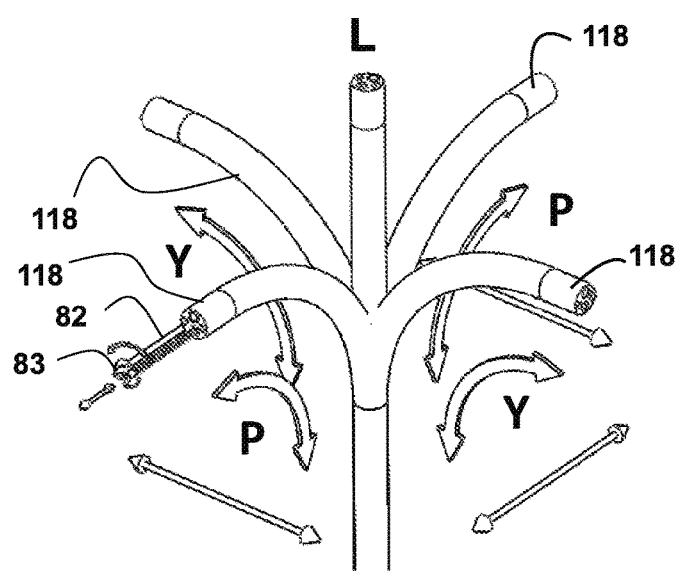
FIGS. 6a-b illustrate actuation of the endoscope tip (FIG. 6a) and a working channel tool (FIG. 6b) via the user interface.

FIGS. 5a-b describe user interface 14 in greater detail. User interface 14 includes a palm interface 16 which is able to pitch (P) and yaw (Y) simultaneously around axis 100 and 101. These rotations are done relative to a ball joint/gimbal pivot point and a sensor mechanism (not shown), located at the top of base 102. In order to control the articulation seamlessly the surgeon places a hand (H) within interface 14 as is shown in FIG. 5b with dorsum interface 17 supporting the back of the surgeon hand as described hereinabove. The resulting movement of the distal tip 118 of endoscope 12 is shown in FIG. 6a. A home (neutral) position of palm interface 16 corresponds to a linear position (L) of distal tip 118, while pitch (P) and yaw (Y) of palm interface 16 results in tip 118 deflection as shown by arrows.

Control over shaft 82 of tool 80 is effected via finger interface 18. Pads 106 of interface 18 are used to control the opening and closing of the jaws. As is shown in FIG. 5b, the index finger and thumb of the surgeon engage pads 106 allowing opening and closing of the jaws by pressing in and releasing pads 106. Rotation of the jaws is controlled by rotating housing 108 around base 113. Interface 18 allows the surgeon to simultaneously control both rotation of the jaws and their opening and closing using two fingers. Housing 108 can also be pulled out and pushed in relative to base 113. A linear sensor located at base 113 of housing 108 allows the surgeon to control the distance the distal end of shaft 82 protrudes from the distal opening 115 (FIG. 6b) of the working channel. The linear sensor may be simple micro switch with 3 contacts (forward backward and neutral) or may be any analog or digital sensor that measures linear travel.

Figure 6B:
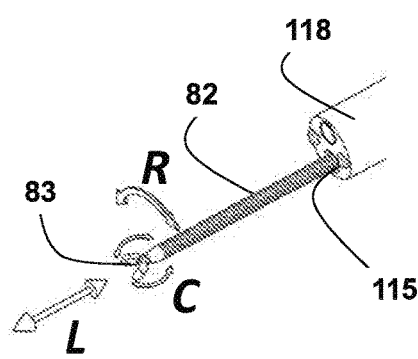

FIG. 6b illustrates shaft rotation (R), grasper closing and opening (C) and shaft translation (L) of tool 80 in response to rotation of housing 108, pressing in and releasing pads 106 and pushing pulling housing 108 (respectively).

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following example, which together with the above descriptions, illustrate the invention in a non limiting fashion.

Testing of a Prototype Control Unit

A prototype of the present control unit was fabricated and tested with a standard flexible endoscope. The prototype included a 3D printed body housing a first drive mechanism for driving endoscope steering via a palm interface and a second drive mechanism for rotating and extending/retracting a grasper tool as well as actuating the jaws thereof.

Figure 7:
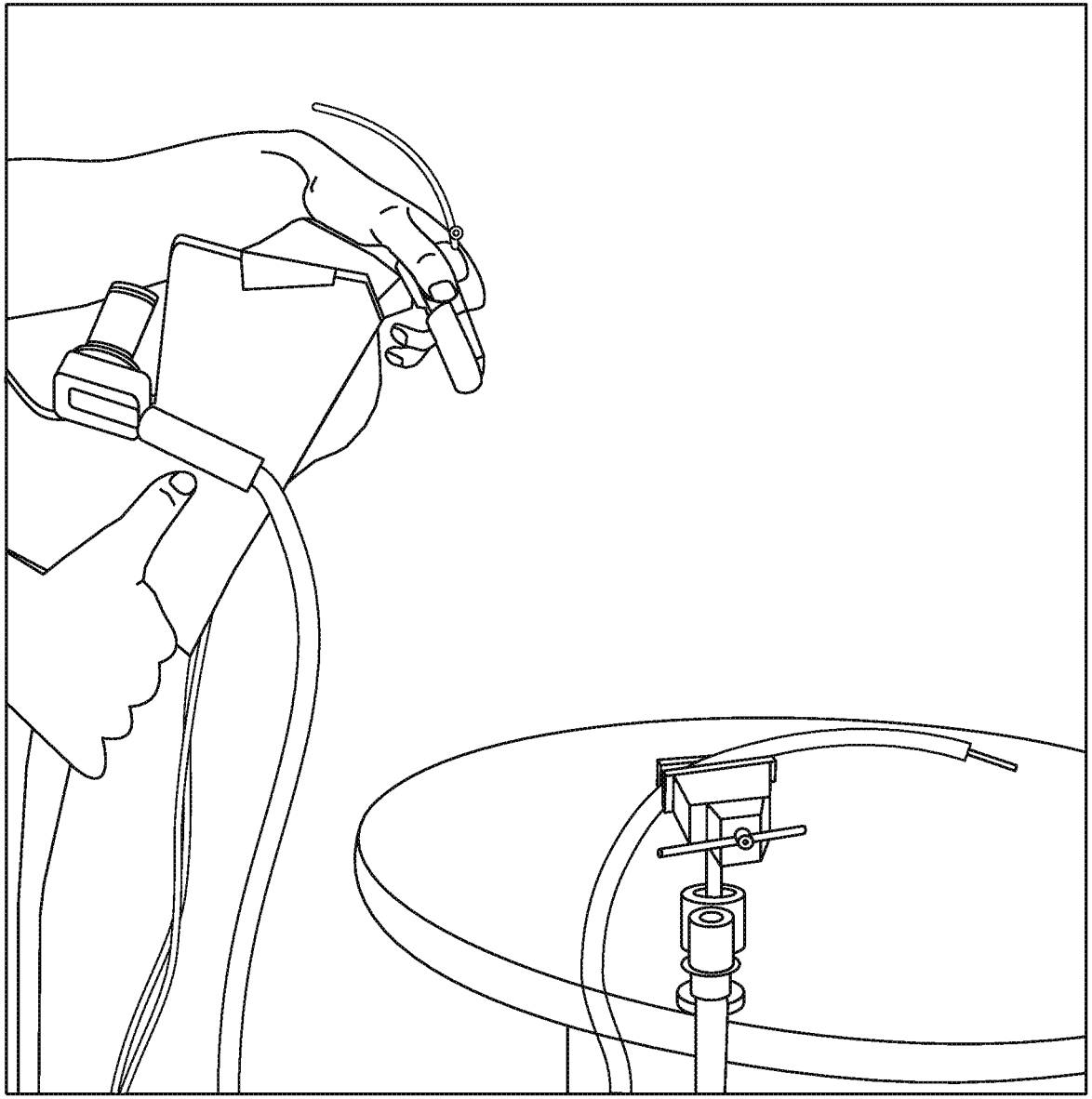
FIG. 7 is an image of a prototype control unit connected to a standard flexible endoscope.

The control unit was attached onto the endoscope and the resulting assembly (FIG. 7) was bench tested for functionality including deflection of the endoscope tip, and actuation of a grasper tool positioned through the working channel of the endoscope.

The user reported smooth and effortless actuation of the endoscope shaft (deflection was tested at 360 degrees) as well as the grasper tool (shaft rotation, tool advancement and retraction and grasper jaw opening and closing). The user was capable of simultaneous deflection of the endoscope shaft and grasper tool actuation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A control unit retrofittable to an external surface of an unmodified endoscope having a shaft deflectable via two manually-operable external rotatable knobs, the control unit comprising:
    (a) a user interface including a first interface being mounted on a pivotal support attached to a housing of the control unit, said first interface being engageable by a palm of a hand;
    (b) a drive unit operable via said user interface, said drive unit being self-enclosed and detachably attached to an external surface of a housing of the endoscope thereby enabling the endoscope to be operated manually through the two manually-operable external rotatable knobs when said drive unit is not attached to the endoscope, said drive unit including a first drive mechanism for engaging the two manually-operable external rotatable knobs thereby allowing a user to control deflection of the shaft of the endoscope via said palm of said hand.

2. The control unit of claim 1, wherein a first rotatable knob of the two rotatable knobs controls up/down deflection of the shaft and a second rotatable knob of the two rotatable knobs controls left/right deflection of the shaft and further wherein said first interface controls both up/down and left/right deflection of the shaft.

3. The control unit of claim 1, wherein said first drive mechanism includes at least one motor operable via said first interface.

4. The control unit of claim 3, wherein said at least one motor operates the two knobs.

5. The control unit of claim 4, wherein said drive mechanism includes a set of gears interposed between said at least one motor and the two knobs.

6. The control unit of claim 1, wherein said drive unit further comprises a second drive mechanism for engaging a manually operable end of a surgical tool positionable through a working channel of the endoscope.

7. The control unit of claim 6, further comprising a second interface being pivotally attached to said first interface and being engageable by one or more fingers of said hand, said second interface being for operating said surgical tool through said second drive mechanism.

8. The control unit of claim 1, further comprising a restraint being pivotally attached to said first interface and having an element capable of elastically deforming to apply a restraining force to a back of said hand when said palm is engaged with said first interface.

9. The control unit of claim 1, wherein said pivotal support is gimbaled.

10. The control unit of claim 7, wherein said second interface includes pads simultaneously operable via thumb and index finger of said hand.

11. The control unit of claim 6, wherein said second drive mechanism includes a servo.

12. The control unit of claim 1, further comprising a third interface for wirelessly controlling a remote device.

13. The control unit of claim 7, wherein said surgical tool includes a steerable shaft and an effector end controllable via said second interface.

* * * * *